United States Patent
Cho et al.

(10) Patent No.: US 9,824,234 B2
(45) Date of Patent: Nov. 21, 2017

(54) METHOD OF PROTECTING CARE INFORMATION IN A CARE PROVIDER TERMINAL

(71) Applicant: LG CNS CO., LTD., Seoul (KR)

(72) Inventors: Chun Rae Cho, Seoul (KR); Jeong Pyo Kim, Seoul (KR); Sung Yong Park, Seoul (KR); Soon Gi Yoon, Seoul (KR); Kwan Pyo Lee, Seoul (KR); Moon Ho Ha, Seoul (KR); Sung Ho Kim, Seoul (KR)

(73) Assignee: LG CNS CO., LTD., Seoul (KR)

( * ) Notice: Subject to any disclaimer, the term of this patent is extended or adjusted under 35 U.S.C. 154(b) by 658 days.

(21) Appl. No.: 14/475,454

(22) Filed: Sep. 2, 2014

(65) Prior Publication Data

US 2016/0063275 A1   Mar. 3, 2016

(51) Int. Cl.

| | | |
|---|---|---|
| *G06F 21/00* | (2013.01) | |
| *G06F 21/62* | (2013.01) | |
| *G06F 19/00* | (2011.01) | |
| *G06F 21/60* | (2013.01) | |
| *H04W 12/06* | (2009.01) | |
| *G06F 21/55* | (2013.01) | |
| *G06F 21/88* | (2013.01) | |

(52) U.S. Cl.
CPC ........ *G06F 21/6245* (2013.01); *G06F 19/322* (2013.01); *G06F 21/554* (2013.01); *G06F 21/602* (2013.01); *G06F 21/88* (2013.01); *H04W 12/06* (2013.01); *G06F 2221/2143* (2013.01); *G06Q 2220/10* (2013.01)

(58) Field of Classification Search
CPC .... G06F 21/6245; G06F 21/554; G06F 21/88; G06F 19/322; G06F 21/602; G06F 2221/2143; H04W 12/06; G06Q 2220/10
See application file for complete search history.

(56) References Cited

U.S. PATENT DOCUMENTS

| | | | | |
|---|---|---|---|---|
| 5,224,496 A | * | 7/1993 | Palmer | .................. G08B 21/22 128/869 |
| 2006/0181153 A1 | * | 8/2006 | Oberle | .................... H02J 9/062 307/112 |
| 2007/0184414 A1 | * | 8/2007 | Perez | ..................... G06Q 50/22 434/1 |
| 2011/0243112 A1 | * | 10/2011 | Misumi | ................. H04W 76/02 370/338 |
| 2011/0254656 A1 | * | 10/2011 | Nurse | ................... A61J 7/0481 340/3.7 |

(Continued)

*Primary Examiner* — Mahfuzur Rahman

(57) ABSTRACT

A method protects care information in a care provider terminal. The method includes detecting if there is a network disconnection between the care provider terminal and an authorized access point (AP), operating the care provider terminal in an offline mode until a first predetermined time is over after the network disconnection is detected, activating an alarm operation when the first predetermined time is over, and deleting the care information when a second predetermined time is over after the alarm operation is activated. The method may further include determining whether or not the care provider terminal is connected to an unauthorized AP while counting the first predetermined time or the second predetermined time, and deleting the care information if it is determined that the care provider terminal is connected to the unauthorized AP.

19 Claims, 8 Drawing Sheets

(56) References Cited

U.S. PATENT DOCUMENTS

| | | | |
|---|---|---|---|
| 2012/0136667 A1 | 5/2012 | Emerick et al. | |
| 2013/0085771 A1* | 4/2013 | Ghanbari | G06Q 10/103 |
| | | | 705/2 |
| 2013/0317753 A1* | 11/2013 | Kamen | G06F 19/3412 |
| | | | 702/19 |
| 2014/0078530 A1* | 3/2014 | Lee | G06F 21/608 |
| | | | 358/1.13 |

* cited by examiner

METHOD OF PROTECTING CARE INFORMATION IN A CARE PROVIDER TERMINAL

BACKGROUND

The background section provided herein is for the purpose of generally presenting the context of the disclosure. Work of the presently named inventors, to the extent the work is described in this section, as well as aspects of the description that may not otherwise qualify as prior art at the time of filing, are neither expressly nor impliedly admitted as prior art against the present disclosure.

In health care settings, such as nursing facilities, care providers are supposed to store patient care records on services provided to patients. In related arts, patient care records are stored by recording a health care professional's verbal notes, which a voice recognition device analyzes. After analyzing the recorded voice, the voice recognition device stores details of the services provided to the patients. These details are used to charge the patient or a guardian thereof for the services afterwards.

U.S. Patent Publication No. 2012/0136667 discloses a voice assistant system for storing a care plan for a resident or patient. In this system, a dedicated device, e.g., a voice assistant device, may provide voice outputs to a user, e.g., a care provider such as a certified nursing assistant (CNA), to provide information on task activities received from a central system. The dedicated device sequentially receives inputs from the user by voice recognition (VR).

According to the related art, information on care services is recorded primarily through text-to-speech (TTS) and speech-to-text (STT) technologies. Thus, if the recorded speech is not clearly recognized by a voice recognition device due to noise or the like, provided services may not be charged. Also, since the voice recognition device analyzes each word, a considerable time may be required for the voice recognition. In addition, since the dedicated device is supposed to operate only in an online state, the dedicated device may not operate normally when a network connection between the dedicated device and the central system is unstable. As a result, it is difficult for the care provider to properly record or charge for care services provided to patients.

In order to overcome the drawbacks of the related art, a point of care documentation solution (POCS) has been introduced. The POCS allows a care provider, such as a CNA, to easily and accurately perform and record care services by checking details of the care services to be provided to patients and storing patient care records on services provided to the patients using a mobile device. The POCS can be implemented in a wireless network environment, and thus can support operations of the mobile device in an offline mode as well as in an online mode.

In the offline mode, e.g., when the mobile device moves to a shadow area, since the mobile device is disconnected from a central system, the care provider uses care information, such as information on patients, information on services to be provided to the patients, and so on, which has been downloaded and stored in a local database of the mobile device so that the care provider can provide the care services to the patients without interruption. However, care information stored in the local database may be exposed to risks such as leakage or illegal use thereof.

BRIEF SUMMARY

Embodiments of the present disclosure relate to methods of protecting care information stored in a database of a care provider terminal and preventing the leakage of care information and the use of the care information in an unauthorized area.

An embodiment of the present disclosure is directed to a method of preventing care information stored in a local database of a care provider terminal from being improperly used in an unauthorized area.

An embodiment of the present disclosure is directed to a method of preventing the leakage of care information stored in a local database of a care provider terminal when the care provider terminal is lost or hacked into.

In accordance with an aspect of the present disclosure, a computer-implemented method of protecting care information in a care provider terminal includes: detecting if there is a network disconnection between the care provider terminal and an authorized access point (AP); operating the care provider terminal in an offline mode until a first predetermined time is over after the network disconnection is detected; activating an alarm operation when the first predetermined time is over; and deleting the care information when a second predetermined time is over after the alarm operation is activated.

The care information may include information on patients and information on care services to be provided to the patients and may be downloaded from a server.

The method may further include: determining whether or not the care provider terminal is connected to an unauthorized AP while counting the first predetermined time or the second predetermined time; and deleting the care information if it is determined that the care provider terminal is connected to the unauthorized AP.

The method may further include: receiving initial settings on the care provider terminal before the care provider terminal is registered to a care provider.

The method may further include: performing installation and activation of a care provider application in the care provider terminal; receiving a password of an administrator through a log-in interface of the activated care provider application; determining whether or not the received password matches a pre-set password; and establishing AP information of the authorized AP in the care provider terminal.

The AP information may include a service set identification (SSID) used to identify the authorized AP.

The method may further include: deactivating a care provider application installed in the care provider terminal while the alarm operation is activated.

The care information may be downloaded from a server and stored in the care provider terminal. The care information may be encrypted when it is stored and may be decrypted when it is read out.

The encryption and decryption of the care information may be performed based on an advanced encryption standard (AES).

In accordance with another aspect of the present disclosure, a care provider terminal of a care provider includes: a memory storing care information downloaded from a server and storing therein instructions; a processor being controlled by the instructions and performing a method; and a timer configured to count a first predetermined time and a second predetermined time sequentially, wherein the method includes detecting if there is a network disconnection between the care provider terminal and an authorized access point (AP), operating the care provider terminal in an offline mode for the first predetermined time if the network disconnection is detected, activating an alarm operation when the first predetermined time is over, and deleting the care information when the second predetermined time is over after the alarm operation is activated.

The method may further include: determining whether or not the care provider terminal is connected to an unauthorized AP while the timer counts the first predetermined time or the second predetermined time; and deleting the care information if it is determined that the care provider terminal is connected to the unauthorized AP.

The method may further include, before the care provider terminal is registered to the care provider: installing and activating a care provider application in the care provider terminal; receiving a password of an administrator through a log-in interface of the activated care provider application; determining whether or not the received password matches a pre-set password; and establishing AP information of the authorized AP in the care provider terminal, wherein the AP information includes a service set identification (SSID) used to identify the authorized AP.

The method may further include: registering an identification and a password of the care provider and a device ID of the care provider terminal to the server to which the care provider terminal is connected via the authorized AP.

In accordance with still another aspect of the present disclosure, a non-transitory computer readable medium has stored thereon a program that, when executed, causes a processor to perform a method, the method including: detecting if there is a network disconnection between a care provider terminal and an authorized access point (AP); operating the care provider terminal in an offline mode until the first predetermined time is over after the network disconnection is detected; activating an alarm operation when the first predetermined time is over; and deleting care information stored in the care provider terminal when a second predetermined time is over after the alarm operation is activated.

The method may further include: determining whether or not the care provider terminal is connected to an unauthorized AP while counting the first predetermined time or the second predetermined time; and deleting the care information if it is determined that the care provider terminal is connected to the unauthorized AP.

The method may further include: installing and activating a care provider application in the care provider terminal; receiving a password of an administrator through a log-in interface of the activated care provider application; determining whether or not the received password matches a pre-set password; and establishing AP information of the authorized AP in the care provider terminal, wherein the AP information includes a service set identification (SSID) used to identify the authorized AP.

The method may further include: registering an identification and a password of a care provider and a device ID of the care provider terminal to a server to which the care provider terminal is connected via the authorized AP.

BRIEF DESCRIPTION OF THE DRAWINGS

Various embodiments of this disclosure will be described with reference to the following figures, wherein like numerals reference like elements, and wherein.

DETAILED DESCRIPTION

The details of one or more embodiments are set forth in the accompanying drawings and the description below. Other features, aspects, and advantages will become apparent from the description, the drawings, and the claims.

Figure 1:
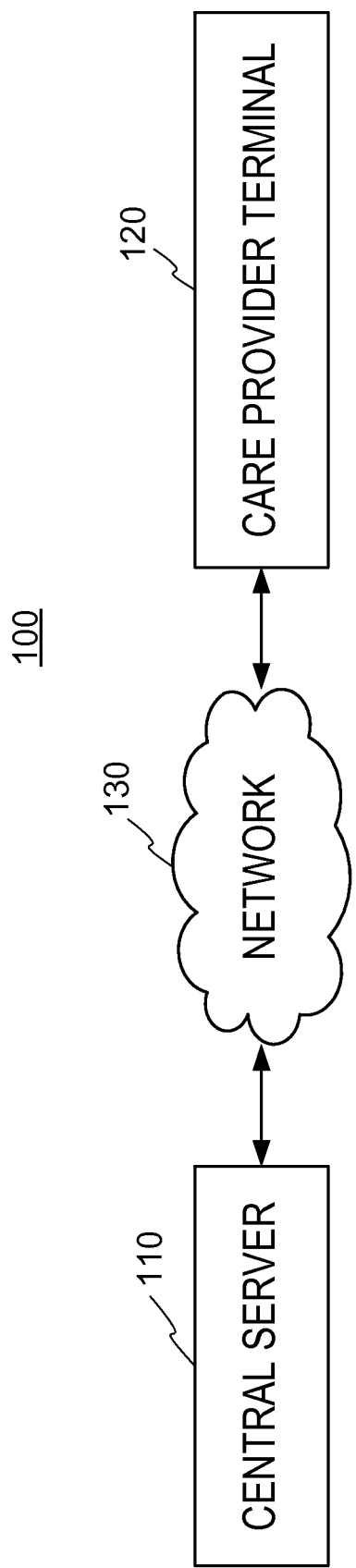
FIG. 1 illustrates a system based on a point of care documentation solution (POCS) in accordance with an embodiment of the present disclosure.

FIG. 1 illustrates a system based on a point of care documentation solution (POCS) in accordance with an embodiment of the present disclosure. The system 100 includes a server 110 (or a patient care documentation server or POCS server) and a care provider terminal 120 (or a patient care documentation device or POCS terminal).

The POCS server 110, which may be a central server, manages care information including information on patients and/or data relating to care tasks that are to be provided to or have been provided to a patient or a person resident at a nursing facility such as sanatorium. Care tasks may include an activities of daily living (ADL) service, a vital service, a restorative service, and the like.

The POCS server 110 is coupled to the POCS terminal 120 via a network 130 to transmit and receive care information, e.g., care task data and/or information on patients, to and from the POCS terminal 120.

In an embodiment, the POCS server 110 is implemented in a cloud computing environment to receive information on a user interface (UI) from the POCS terminal 120.

In an embodiment, the POCS server 110 transmits and receives a dynamic document to and from the POCS terminal 120 through a software architecture (e.g., Restful API), and generates patient care documentation based on the dynamic document from the POCS terminal 120.

The POCS terminal 120 may provide a touch sensitive user interface, e.g., a touchscreen, to a user. In an implementation, the user is a care provider. Care task data, including user-undertaken care tasks, are managed through the user interface on the basis of a point of care document (POCD). Herein, the user may be a health care professional, such as a certified nursing assistant (CNA), who provides care services to a patient or person resident at a nursing facility such as a sanatorium.

In an embodiment, the POCS terminal 120 is coupled to the POCS server 110 via the network 130. The POCS terminal 120 may include any mobile computing device that is suitable for providing patient care documentation. The mobile computing device may be a mobile device such as a mobile phone (smart phone), a personal digital assistant (PDA), a notebook, a tablet personal computer (PC), or the like. In an embodiment, the POCS terminal 120 is operable in the cloud computing environment. For example, one or more software aspects of the patient document may be provided in the cloud and may be accessed by a physical computing device being used by a user to implement various embodiments of the present invention.

The network 130 may be a wired or wireless communication network. Examples of the wireless network include Wi-Fi, 3G, and LTE.

The system 100 can support operations of a mobile device, which is used as the POCS terminal 120, in an offline mode as well as in an online mode. In the online mode, the POCS terminal 120 can communicate with the POCS server 110 in real time since the POCS terminal 120 is connected to the POCS server 110 via the network 130. Thus, the care provider can provide care services to patients based on care information that is transmitted from the POCS server 110 in real time, without interruption.

On the other hand, in the offline mode, the POCS terminal 120 cannot communicate with the POCS server 110 in real time since the POCS terminal 120 is disconnected from the POCS server 110. Therefore, to allow the care provider to continue to perform care services without interruption, care information is downloaded and stored in a storage of the POCS terminal 120, i.e., a local database, when the POCS terminal 120 is connected to the POCS server 110. As a result, even if the POCS terminal 120 is disconnected from the POCS server 110, the POCS terminal 120 can continue to operate in the offline mode to allow the care provider to check the details of the care services to be provided to patients and store patient care records on care services provided to the patients using the POCS terminal 120, and thus the care provider can continue to provide the care services without interruption based on the care information stored in the local database.

However, when the care information is downloaded and stored in the local database of the POCS terminal 120, the care information may be leaked and/or illegally used due to improper use of the POCS terminal 120. Therefore, embodiments of the present disclosure provide methods of protecting care information stored in the storage of the POCS terminal 120. Methods in accordance with embodiments will be described with reference to FIGS. 2-7.

Figure 2:
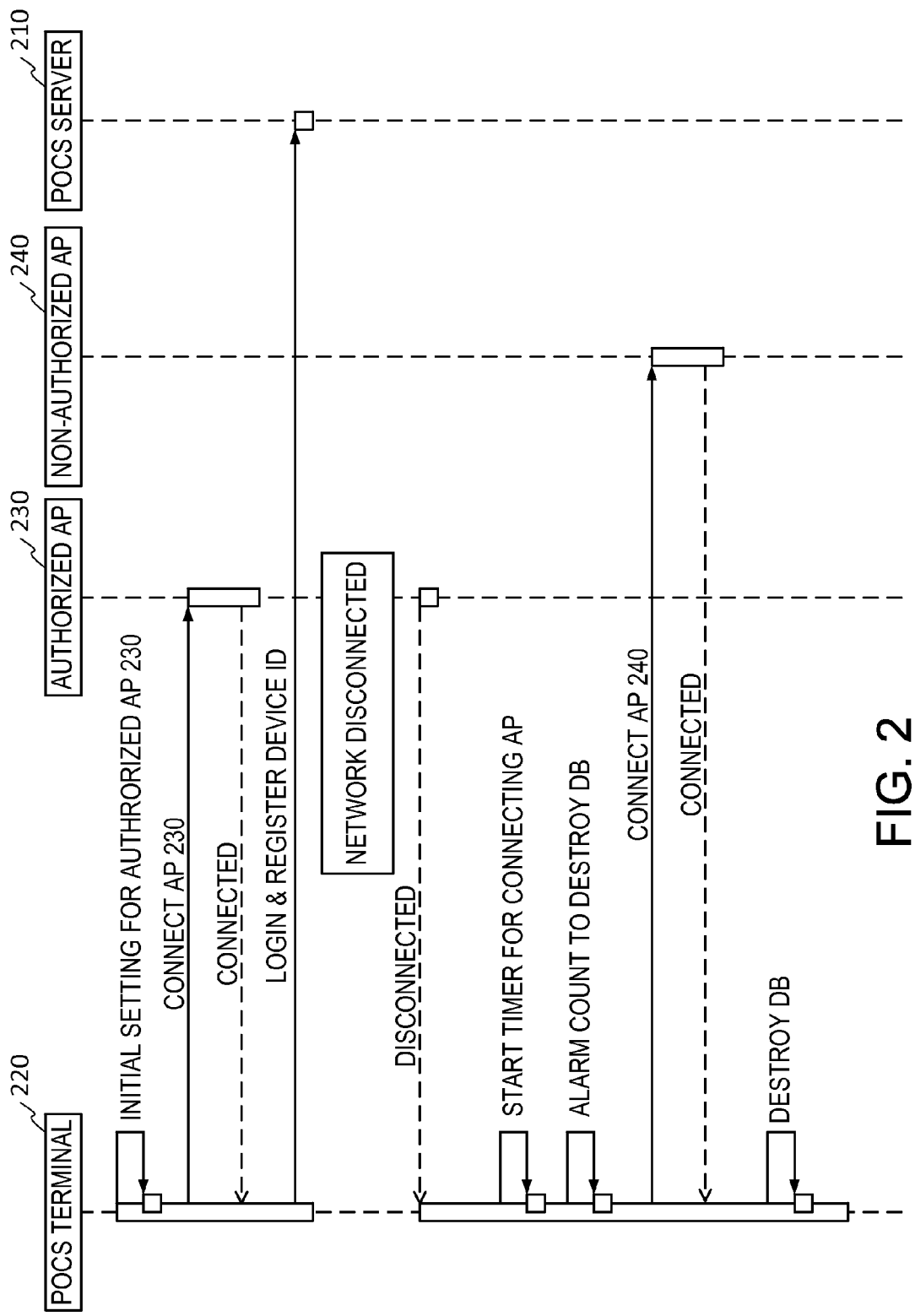
FIG. 2 is a flow diagram illustrating a method of preventing care information from being used in an unauthorized area in accordance with an embodiment of the present disclosure.

FIG. 2 is a flow diagram illustrating a method of preventing care information stored in a local database of a POCS terminal from being leaked and/or used in an unauthorized area in accordance with an embodiment of the present disclosure. For illustrative convenience, FIG. 2 refers to a POCS terminal 220 in which a care provider application, e.g., POCS application, is installed, a POCS server 210, an authorized access point (AP) 230, and an unauthorized AP 240. The POCS terminal 220 accesses the authorized AP 230 or the non-authorized AP 240 via the network 130 in order to communicate with the POCS server 210.

Before the POCS terminal 220 is handed out or given to a care provider, initial settings of the POCS terminal 220 are established by an administrator. In the initial settings, AP information of the authorized AP 230 is stored in the POCS terminal 220. As a result, the POCS terminal 220 is set to be used only in an authorized area, e.g., the nursing facility, which is included in coverage of the authorized AP 230. The AP information of the authorized AP 230 may include a service set identification (SSID) for distinguishing the authorized AP 230 from other APs, including the unauthorized AP 240. To establish the initial settings of the POCS terminal 220, the POCS application displays an interface for the initial settings on the screen of the POCS terminal 220 that receives an ID and a password from the administrator. That is, only the administrator is authorized to establish the initial settings of the POCS terminal 220, since access to the initial settings interface is restricted to an administrator with the ID and password.

After the initial settings are completed, the POCS terminal 220 is given to the care provider. After that, the care provider uses the POCS terminal 220 to access the POCS server 210 via the authorized AP 230. Once the POCS terminal 220 is connected to the POCS server 210 via the authorized AP 230, the POCS terminal 220 transmits registration information to the POCS server 210. The registration information is stored in the POCS server 210. The registration information may include a device ID of the POCS terminal 220, a login ID and a password of the care provider, and so on. After the care provider logs in to the POCS server 210 using the POCS terminal 220 and the registration information, care information is downloaded from the POCS server 210 and stored in the local database of the POCS terminal 220. As a result, the care provider can provide care services to patients based on the care information stored in the local database. In an embodiment, the care information stored in the local database may be regularly updated while the POCS terminal 220 is connected to the POCS server 210.

While the POCS terminal 220 is connected to the authorized AP, the care provider can provide the care services to the patients without interruption based on regularly updated care information. On the other hand, if the POCS terminal 220 is disconnected from the POCS server 210, because, for example there is a network disconnection between the POCS terminal 220 and the authorized AP 230 when the POCS terminal 220 is out of the range of the coverage of the authorized AP 230, the network disconnection is detected by the POCS terminal 220.

If a network disconnection between the POCS terminal 220 and the authorized AP 230 is detected, a timer (not shown) in the POCS terminal 220 starts to count a first predetermined time. During this time, the POCS terminal 220 may operate in an offline mode, and thus the care provider can provide the care services without interruption using the POCS application that is still working. While the timer counts the first predetermined time, if the POCS terminal 220 is connected to the unauthorized AP 240, the connection is detected and, as a result, the care information stored in the local database is deleted or destroyed. In addition, in an embodiment, the POCS application may be deactivated or stop working when a connection between the POCS terminal 220 and the unauthorized AP 240 is detected. As a result, the care provider cannot access the care information any more since the care information stored in the local database is deleted and/or the POCS application is deactivated or stops working.

Meanwhile, if there is a network disconnection between the POCS terminal 220 and the authorized AP 230 that the network disconnection continues until the first predetermined time is over and there is no connection between the POCS terminal 220 and the unauthorized AP 240, the timer starts to count a second predetermined time. While the timer counts the second predetermined time, an alarm operation is performed to inform the care provider that the first predetermined time is over and/or the POCS terminal 220 should be re-connected to the authorized AP 230. While the timer counts the second predetermined time, if the POCS terminal 220 is connected to the unauthorized AP 240, the care information stored in the local database is deleted or destroyed. In an embodiment, even if there is no connection between the POCS terminal 220 and the unauthorized AP 240, the care information stored in the local database is automatically deleted or destroyed after the second predetermined time is over if the POCS terminal 220 has not been connected to the authorized AP 230.

Embodiments of operations described with reference to FIG. 2 will be described in more detail with reference to flowcharts shown in FIGS. 3-5.

Figure 3:
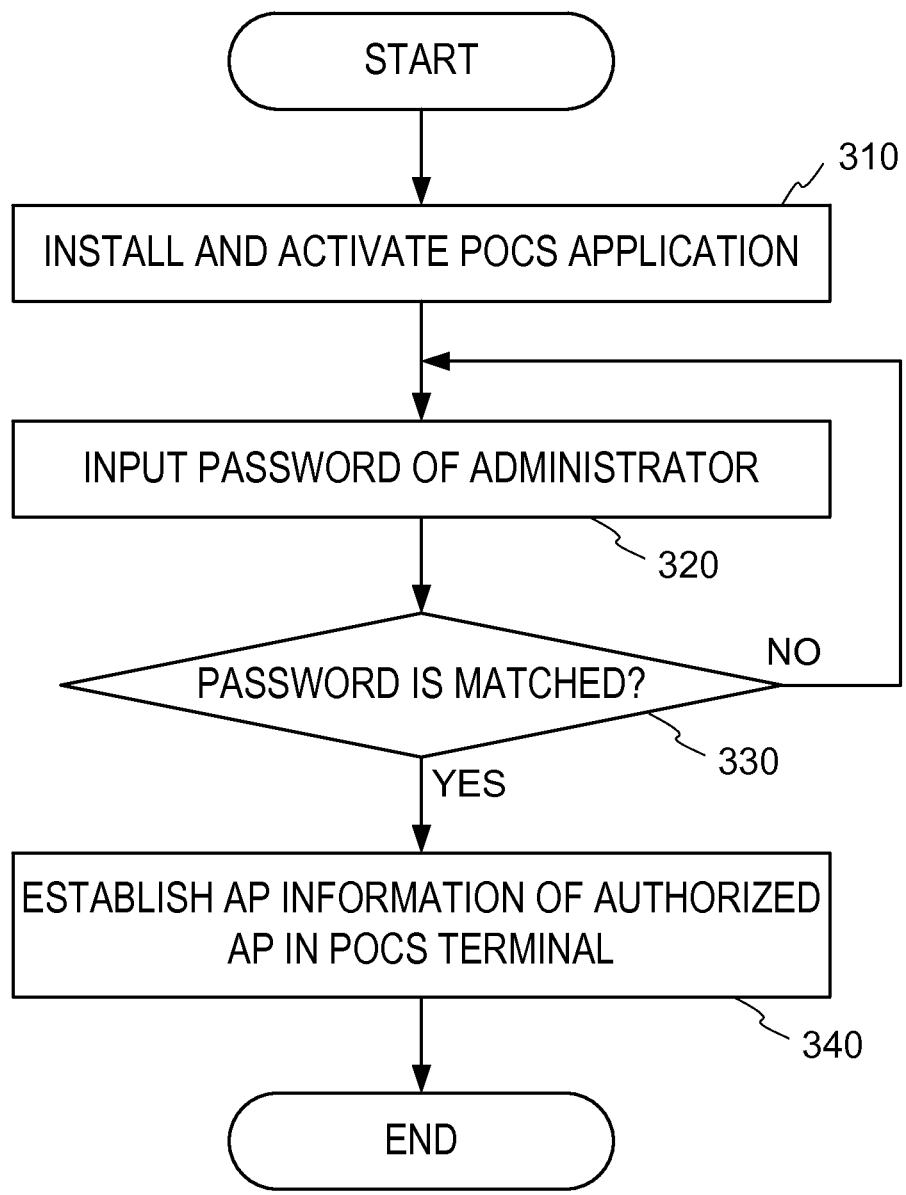
FIG. 3 is a flowchart illustrating initial settings of a care provider terminal for use in an authorized area in accordance with an embodiment of the present disclosure.

FIG. 3 is a flowchart illustrating initial settings of a POCS terminal for the use in an authorized area in accordance with an embodiment of the present disclosure.

At step 310, an installation and activation process of a POCS application is performed in the POCS terminal 220 to establish the initial settings on the POCS terminal 220 before giving the POCS terminal 220 to a care provider.

If the POCS application is activated at step 310 and then a log-in interface is provided and the POCS terminal 220 receives at least an administrator's password, which is input through the log-in interface at step 320.

At step 330, it is determined whether or not the inputted password matches a pre-set password. This process is used to restrict the authority to establish the initial settings to only the administrator. The password may be set when the POCS application is installed in the POCS terminal 220. However, embodiments are not limited thereto.

If it is determined that the inputted password does not match the pre-set password, the procedure returns to step 320. On the other hand, if it is determined that the inputted password matches the pre-set password, at step 340, input AP information of the authorized AP 230 is received in the POCS terminal 220 to set the POCS terminal 220 to be used only in an authorized area included in the coverage of the authorized AP 230. The AP information may include a service set identification (SSID) used to identify the authorized AP 230. If the AP information is established in the POCS terminal 220, the initial settings for the POCS terminal 220 may be completed, and the POCS terminal 220 is ready to be given to a care provider.

Figure 4:
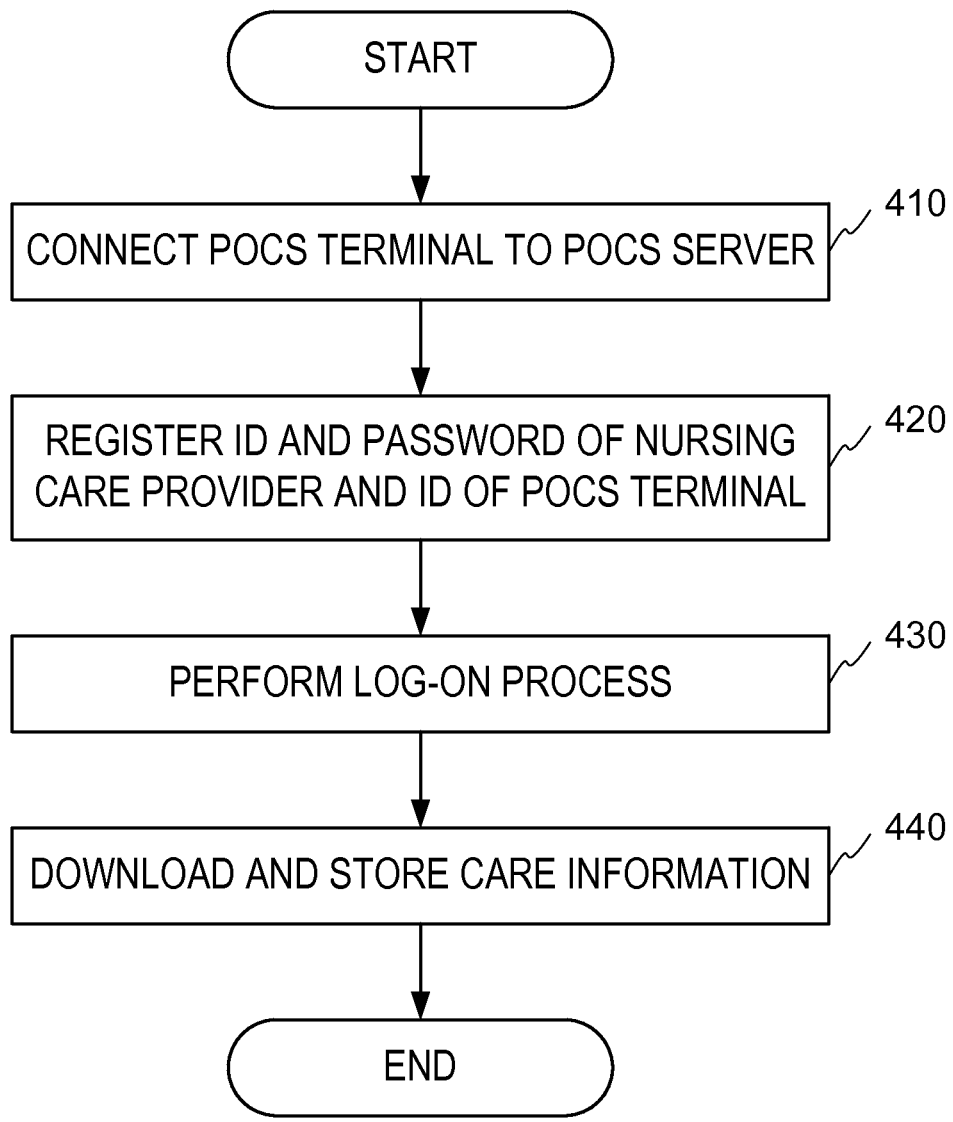
FIG. 4 is a flowchart illustrating a registration and log-in process of a care provider terminal in accordance with an embodiment of the present disclosure.

FIG. 4 is a flowchart illustrating a registration process and a log-in process of a POCS terminal in accordance with an embodiment of the present disclosure. If the POCS terminal 220 is initialized by the procedure illustrated in FIG. 3, the administrator may give the POCS terminal 220 to a care provider.

After the care provider receives the initialized POCS terminal 220, which includes the initial settings, a registration process is performed by connecting the POCS terminal 220 to the POCS server 210 via the authorized AP 230.

At step 410, the POCS terminal 220 is connected to the POCS server 210 via the authorized AP 230. If the POCS terminal 220 is connected to the POCS server 210, an ID and password of the care provider is registered with the POCS server 210 at step 420. The ID and password of the care provider are stored in a storage of the POCS server 210. In an embodiment, an ID of the POCS terminal 220 is also stored in the storage of the POCS server 210 during the registration process.

After the registration process is completed, at step 430, a log-in process is performed to log the POCS terminal 220 of the care provider in to the POCS server 210. As a result, the care provider can access care information stored in the POCS server 210 using the POCS terminal 220.

After that, at step 440, care information may be downloaded from the POCS server 210, and the downloaded care information is stored in the storage of the POCS terminal 220, i.e., the local database. In an offline mode, the care information stored in the local database is used to allow the care provider to fulfill care tasks based thereon without interruption.

Figure 5:
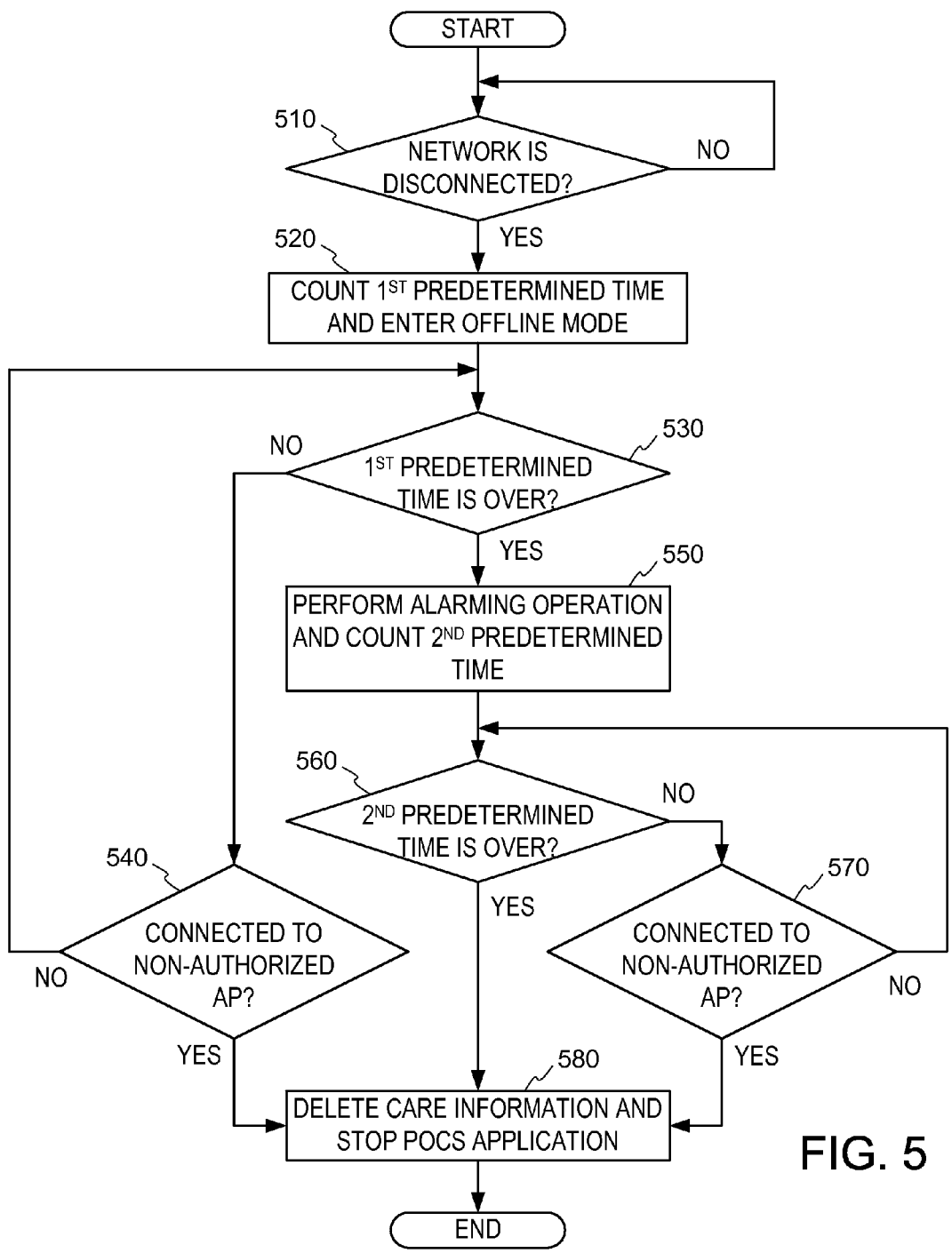
FIG. 5 is a flowchart illustrating a method of preventing care information from being used in an unauthorized area in accordance with an embodiment of the present disclosure.

FIG. 5 is a flowchart illustrating a method of preventing care information from being used in an unauthorized area in accordance with an embodiment of the present disclosure. Care information stored in the storage of the POCS terminal 220 may be exposed to risks such as the leakage or illegal use thereof. Therefore, in order to protect the care information, the method shown in FIG. 5 is introduced.

Referring to FIG. 5, at step 510, whether or not the POCS terminal 220 is disconnected from the authorized AP 230 is detected. The network disconnection between the POCS terminal 220 and the authorized AP 230 may occur as the care provider holding the POCS terminal 220 moves to a radio shadow area or an unauthorized area included in coverage of the unauthorized AP 240.

If a network disconnection is detected at step 510, a timer in the POCS terminal 220 starts to count a first predetermined time at step 520, and the POCS terminal 220 enters an offline mode.

At step 530, it is determined whether the first predetermined time is over or not. If it is determined that the first predetermined time is not over at step 530, while the timer counts the first predetermined time, it is determined whether or not the POCS terminal 220 is connected to the unauthorized AP 240 at step 540.

If it is determine that the POCS terminal 220 is not connected to the unauthorized AP 240 at step 540, the procedure returns to step 530.

If it is determined that the first predetermined time is over, at step 550, an alarm operation is performed to notify the care provider that the first predetermined time is over and/or the POCS terminal 220 should be re-connected to the authorized AP 230 before a second predetermined time passes. At the same time, the timer starts to count the second predetermined time. In an embodiment, during the alarm operation, an alarming screen is displayed on a display of the POCS terminal 220, and the POCS application is deactivated or stops working. As a result, the care provider cannot use the POCS application while the alarming screen is displayed.

At step 560, it is determined whether the second predetermined time is over or not. If it is determined that the second predetermined time is not over at step 560, while the timer counts the second predetermined time, it is determined whether or not the POCS terminal 220 is connected to the unauthorized AP 240 at step 570.

If it is determined that the POCS terminal 220 is connected to the unauthorized AP 240 at step 540 or step 570 or if it is determined at step 560 that the second predetermined time is over, care information, which has been downloaded from the POCS server 210 and is stored in the storage of the POCS terminal 220, is destroyed, i.e., deleted. As a result, it is possible to prevent the care information stored in the POCS terminal 220 from being used in the unauthorized area included in the coverage of the unauthorized AP 240. The unauthorized area may be distanced from the nursing facility, which is included in the authorized area. In an embodiment, the first and second predetermined times may be set by the administrator when the initial settings of the POCS terminal 220 are established. However, embodiments are not limited thereto.

Figure 6:
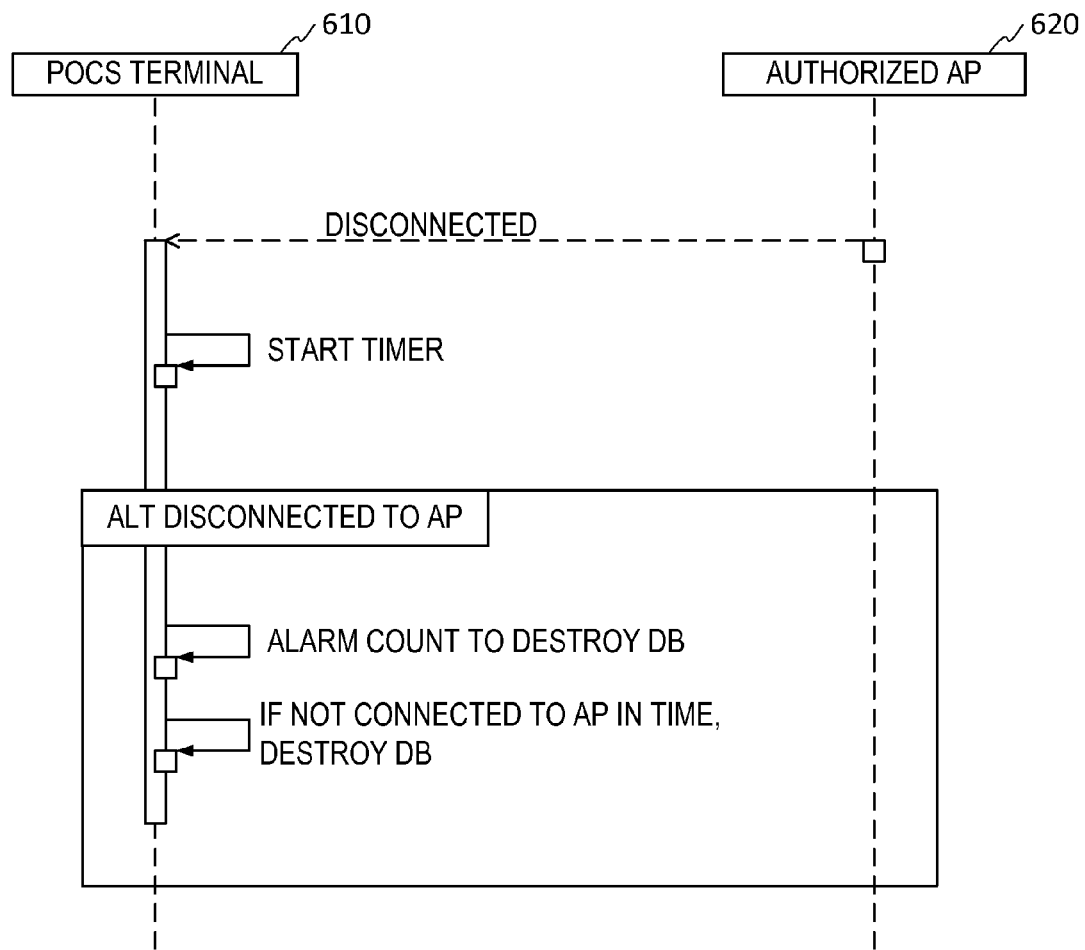
FIG. 6 is a flow diagram illustrating a method of preventing the leakage of care information during a network disconnection after a critical time in accordance with an embodiment of the present disclosure.

FIG. 6 is a flow diagram illustrating a method of protecting care information stored in a storage of a POCS terminal during a network disconnection after a critical time, in accordance with an embodiment of the present disclosure.

For illustrative convenience, FIG. 6 refers to a POCS terminal 610 in which a POCS application is installed and an authorized AP 620. The POCS terminal 610 is connected to the authorized AP 620 via a network in order to communicate with a POCS server.

A care provider is supposed to stay in an authorized area such as a sanatorium. However, if the care provider moves to a radio shadow area or to an area outside of the authorized area, a network disconnection may occur between the POCS terminal 610 and an authorized AP 620.

Therefore, if the network disconnection is detected, a timer (not shown) in the POCS terminal 610 starts to count a first predetermined time. If the POCS terminal 610 is not connected to the authorized AP 620 by the time the first predetermined time has passed, the timer starts to count a second predetermined time and an alarm operation is activated to notify the care provider that the first predetermined time is over and/or the POCS terminal 610 should be re-connected to the authorized AP 620.

If the POCS terminal 610 is not re-connected to the authorized AP 620 by the time the second predetermined time has passed, the care information stored in the local database is automatically deleted or destroyed after the second predetermined time is over, thereby preventing illegal or improper use or leakage of the care information in an unauthorized area outside of the authorized area.

Figure 7:
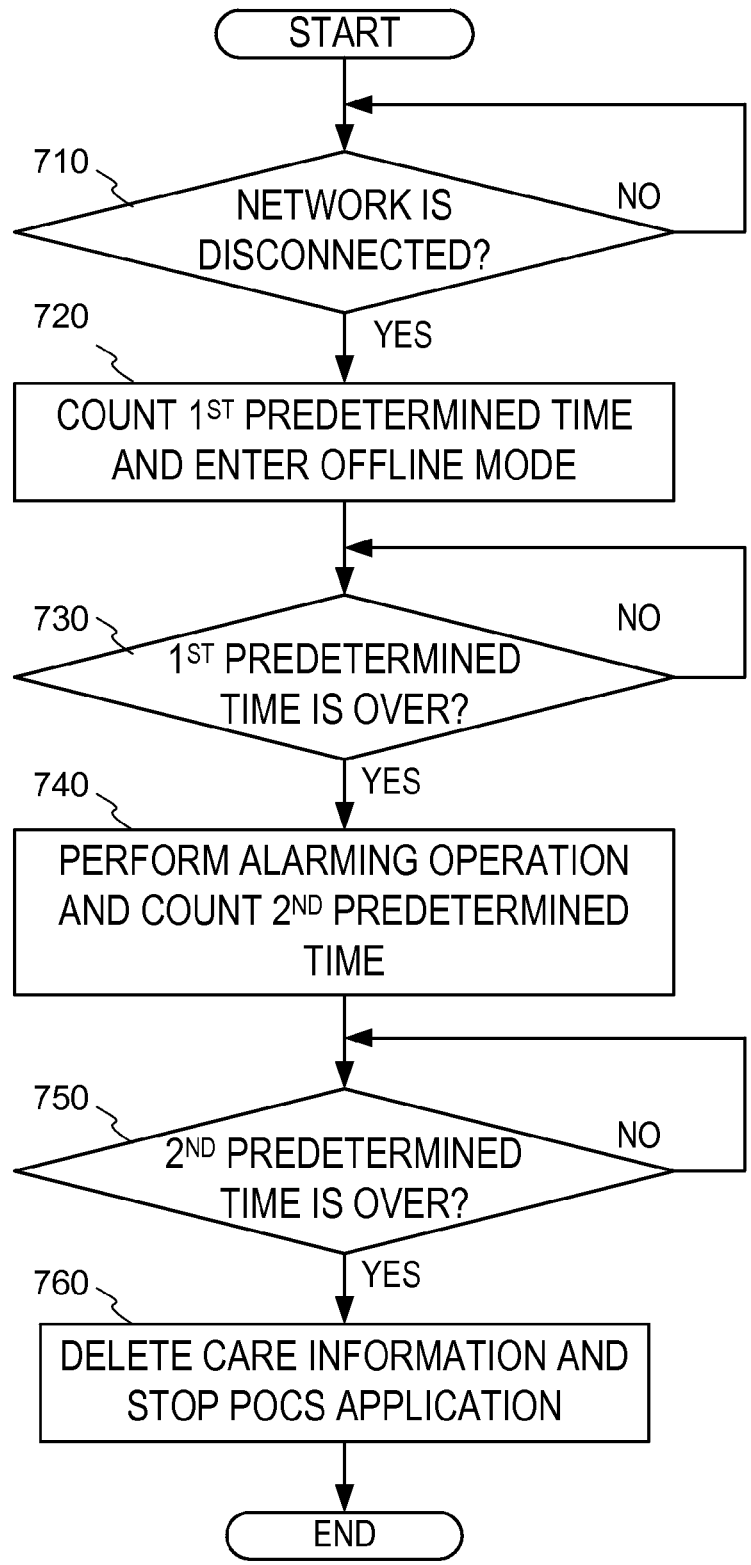
FIG. 7 is a flowchart illustrating details of a method of preventing the leakage of care information during a network disconnection after a critical time in accordance with an embodiment of the present disclosure.

FIG. 7 is a flowchart illustrating details of a method of preventing the leakage of care information stored in a storage of a POCS terminal during a network disconnection after a critical time, in accordance with an embodiment of the present disclosure. The method of FIG. 7 will be described with reference to FIG. 6.

At step 710, it is determined whether there is a network disconnection between the POCS terminal 610 and the authorized AP 620. If the POCS terminal 610 is determined to be disconnected from the authorized AP 620, at step 720, a timer in the POCS terminal 610 starts to count a first predetermined time, and, at the same time, the POCS terminal 610 enters an offline mode. In the offline mode, a care provider can perform care tasks without interruption based on care information stored in the storage of the POCS terminal 610.

At step 730, it is determined whether or not the first predetermined time is over. If the first predetermined time is over, at step 740, the timer starts to count a second predetermined time, and an alarm operation is performed to notify the care provider that the first predetermined time is over and/or the POCS terminal 610 should be re-connected to the authorized AP 620. In an embodiment, during the alarm operation, an alarming screen is displayed on a display of the POCS terminal 610, and the POCS application is deactivated or stops working.

After that, at step 750, it is determined whether or not the second predetermined time is over. If it is determined that the second predetermined time is over, at step 760, the care information stored in the local database is deleted or destroyed, and the POCS application is deactivated or stops working. As a result, it is possible to prevent the improper or illegal use of the care information stored in the local database in the unauthorized area, which is not included in the coverage of the authorized AP 620. In addition, it is possible to prevent the care information from being leaked when the network disconnection between the POCS terminal 610 and the authorized AP 620 continues for a critical time corresponding to a sum of the first and second predetermined times. The first and second predetermined times may be pre-set by an administrator before the POCS terminal 610 is handed out to the care provider.

Figure 8:
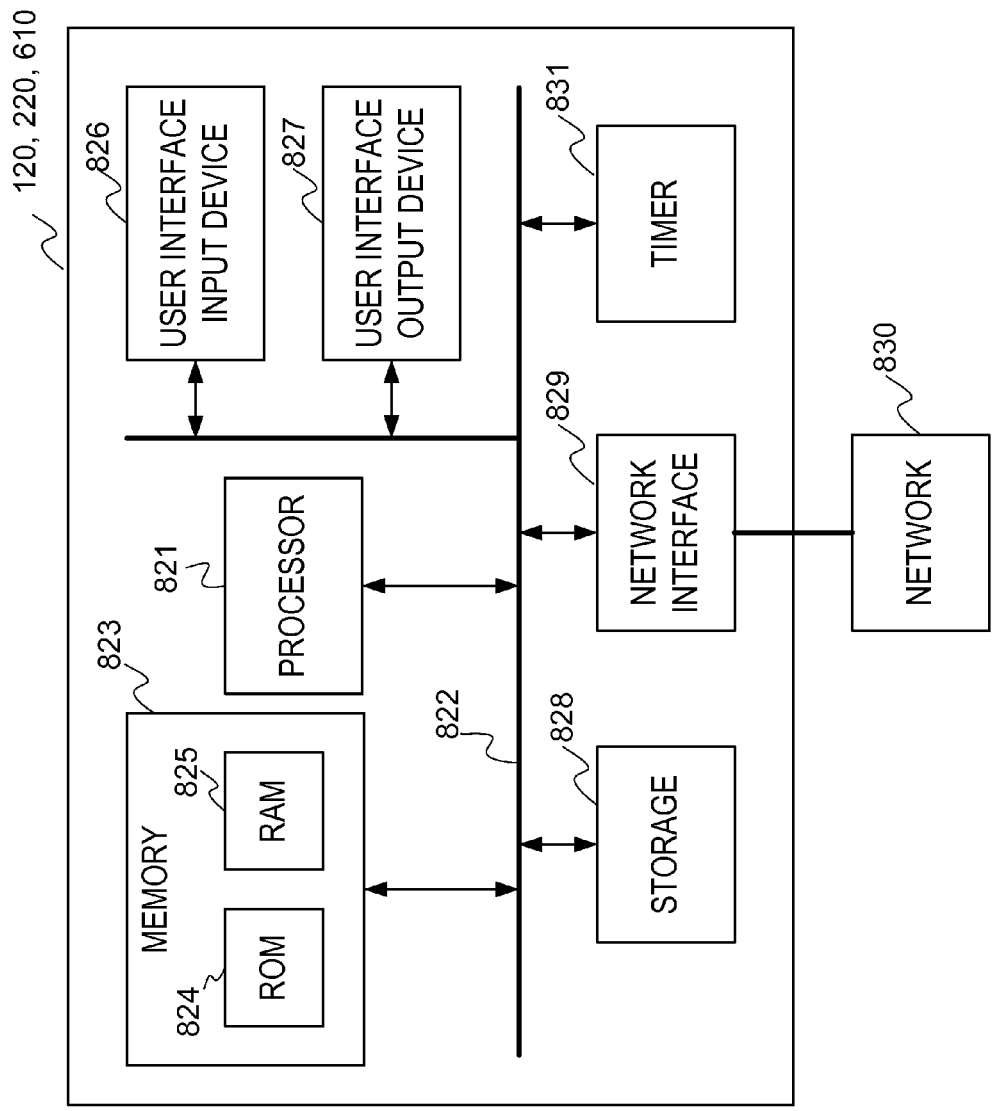
FIG. 8 illustrates a block diagram of a care provider terminal in accordance with an embodiment of the present disclosure.

FIG. 8 illustrates a simplified view of a POCS terminal in accordance with an embodiment of the present disclosure.

The POCS terminal 120 (or 220 or 610) includes a processor or CPU 821 that is in communication with a variety of other components via a bus 822. Such other components of the POCS terminal 120 include, but are not limited to, a non-transitory computer readable storage medium as a memory 823, including a read only memory (ROM) 824 and a random access memory (RAM) 825, and also a higher capacity non-transitory computer readable storage medium 828 that acts as a local database.

One or more of these components may be employed by the POCS terminal 120 to store computer code including instructions for patient care documentation. This computer code may be received from the POCS server 110 over the network 130 to allow a user, e.g., a care provider, to provide and receive information relating to the patient care documentation, care information, and so on.

The user may communicate with the POCS terminal 120 via a user interface input device 826 such as a keyboard, pointing devices such as a mouse, trackball, touchpad, or graphics tablet, a scanner, a barcode scanner for scanning item barcodes, a touchscreen incorporated into a display, or other types of input devices. In general, use of the term "input device" is intended to include all possible mechanisms for inputting information into the POCS terminal 120 or onto the network 130.

The user may receive information from the POCS terminal 120 via a user interface output device 827. The user interface output device 827 may include a visual output device, such as a display screen, but is not limited thereto. The term "output device" is intended to include all possible mechanisms for outputting information to a user, and may include a visual output device alone, or in combination with any of an auditory output device, such as a speaker, and a haptic output device. Information output to the user may include information on the patient care documentation, which includes care information such as information on patients, information on services to be provided to the patients, and so on.

In an embodiment, the display screen may be a touchscreen that both displays the information from the POCS terminal 120 and receives inputs from the user. That is, the display screen may act as a user interface input device and a user interface output device. In an embodiment, the POCS terminal 120 may include a sensing unit (not shown) that senses inputs provided through, for example, a touchscreen, including but not limited to swiping motions made on the touchscreen.

The POCS terminal 120 also includes a network interface element 829. This network interface element 829 is configured to allow information to be communicated between the POCS terminal 120 and the network 130. Such information may include the code that is executable on the POCS terminal 120, care task data from the POCS server 110, and records on care tasks applied to the patients.

The POCS terminal 120 further includes a timer 831 to count a predetermined time when the POCS terminal 120 is disconnected from an authorized AP. The predetermined time may include a first predetermine time during which the POCS terminal 120 operates in an offline mode or a second predetermined time during which an alarm operation is activated to notify the user that the first predetermined time is over and/or the POCS terminal 120 should be re-connected to the authorized AP.

The processor 821 may perform the methods described with reference to FIGS. 2-7 in cooperation with other components illustrated in FIG. 8. The care information may be stored in the storage 828.

In accordance with embodiments of the present disclosure, to protect care information stored in a local database, e.g., the storage 828 in FIG. 8, when a POCS terminal is lost or hacked into, the care information may be encrypted when it is stored in the local database and decrypted when it is read out of the local database and displayed on a display, e.g., the user interface output device 827 in FIG. 8.

In an embodiment, an advanced encryption standard (AES) may be used for the encryption and decryption of the care information, and the care information may be encrypted and decrypted by DB column units. As a result, although a DB file is extracted by hacking of the POCS terminal, a user cannot recognize the care information since the care information is encrypted/decrypted at a DB interface layer. The encryption/decryption may be performed using pre-defined symmetric keys.

In accordance with embodiments of the present disclosure, the foregoing methods may be implemented as code that can be read by a computer and stored on a non-transitory computer-readable medium. The computer-readable medium may include any type of recording device in which data that can be read by a computing system is stored. The computer-readable medium may include a ROM, a RAM, a CD-ROM, a magnetic tape, a floppy disk, an optical data storage device, and the like. The computer-readable medium may be distributed over network-coupled computer systems so that the computer-readable code may be stored and executed in a distributed fashion.

The broad teachings of the present disclosure can be implemented in a variety of forms. Therefore, while this disclosure includes particular examples, the true scope of the disclosure should not be so limited since other modifications will become apparent upon a study of the drawings, the specification, and the following claims.

What is claimed is:

1. A computer-implemented method of protecting care information in a care provider terminal, the method comprising:
    detecting if there is a network disconnection between the care provider terminal and an authorized access point (AP);
    operating the care provider terminal in an offline mode until a first predetermined time is over while the network disconnection is maintained after the network disconnection is detected;
    activating an alarm operation when the first predetermined time is over while the network disconnection is maintained, the alarm operation being performed to inform a care provider that the first predetermined time is over; and
    deleting the care information when a second predetermined time is over while the network disconnection is maintained after the alarm operation is activated,
    wherein the care provider terminal has AP information, the AP information including a service set identification (SSID) used to identify the authorized AP.

2. The method of claim 1, wherein the care information includes information on patients and information on care services to be provided to the patients and is downloaded from a server.

3. The method of claim 1, further comprising:
    determining whether or not the care provider terminal is connected to an unauthorized AP while counting the first predetermined time or the second predetermined time; and
    deleting the care information if it is determined that the care provider terminal is connected to the unauthorized AP.

4. The method of claim 1, further comprising:
    receiving initial settings on the care provider terminal before the care provider terminal is registered to the care provider.

5. The method of claim 4, further comprising:
    performing installation and activation of a care provider application in the care provider terminal;
    receiving a password of an administrator through a log-in interface of the activated care provider application;
    determining whether or not the received password matches a pre-set password; and
    establishing AP information of the authorized AP in the care provider terminal.

6. The method of claim 1, further comprising:
    registering an identification and a password of the care provider and a device ID of the care provider terminal to a server to which the care provider terminal is connected via the authorized AP.

7. The method of claim 1, wherein the first and second predetermined times are determined before the care provider terminal is registered to the care provider.

8. The method of claim 1, further comprising:
    deactivating a care provider application installed in the care provider terminal while the alarm operation is activated.

9. The method of claim 1, wherein the care information is downloaded from a server and stored in the care provider terminal, and
    wherein the care information is encrypted when it is stored and decrypted when it is read out.

10. The method of claim 9, wherein the encryption and decryption of the care information are performed based on an advanced encryption standard (AES).

11. A care provider terminal of a care provider, comprising:
    a memory storing care information downloaded from a server and storing therein instructions;
    a processor being controlled by the instructions and performing a method, the method comprising:
        detecting if there is a network disconnection between the care provider terminal and an authorized access point (AP);
        operating the care provider terminal in an offline mode for a first predetermined time while the network disconnection is maintained;
        activating an alarm operation when the first predetermined time is over while the network disconnection is maintained, the alarm operation being performed to inform the care provider that the first predetermined time is over; and
        deleting the care information when a second predetermined time is over while the network disconnection is maintained after the alarm operation is activated; and
    a timer configured to count the first predetermined time and the second predetermined time sequentially,
    wherein the care provider terminal has AP information, the AP information including a service set identification (SSID) used to identify the authorized AP.

12. The care provider terminal of claim 11, wherein the care information includes information on patients and information on care services to be provided to the patients.

13. The care provider terminal of claim 11, wherein the method further comprises:
  determining whether or not the care provider terminal is connected to an unauthorized AP while the timer counts the first predetermined time or the second predetermined time; and
  deleting the care information if it is determined that the care provider terminal is connected to the unauthorized AP.

14. The care provider terminal of claim 11, wherein the method further comprises, before the care provider terminal is registered to the care provider:
  installing and activating a care provider application in the care provider terminal;
  receiving a password of an administrator through a log-in interface of the activated care provider application;
  determining whether or not the received password matches a pre-set password; and
  establishing the AP information of the authorized AP in the care provider terminal.

15. The care provider terminal of claim 11, wherein the method further comprises:
  registering an identification and a password of the care provider and a device ID of the care provider terminal to the server to which the care provider terminal is connected via the authorized AP.

16. A non-transitory computer readable medium having stored thereon a program that, when executed, causes a processor to perform a method, the method comprising:
  detecting if there is a network disconnection between a care provider terminal and an authorized access point (AP);
  operating the care provider terminal in an offline mode until the first predetermined time is over while the network disconnection is maintained after the network disconnection is detected;
  activating an alarm operation when the first predetermined time is over while the network disconnection is maintained, the alarm operation being performed to inform a care provider that the first predetermined time is over; and
  deleting care information stored in the care provider terminal when a second predetermined time is over while the network disconnection is maintained after the alarm operation is activated,
  wherein the care provider terminal has AP information, the AP information including a service set identification (SSID) used to identify the authorized AP.

17. The non-transitory computer readable medium of claim 16, wherein the method further comprises:
  determining whether or not the care provider terminal is connected to an unauthorized AP while counting the first predetermined time or the second predetermined time; and
  deleting the care information if it is determined that the care provider terminal is connected to the unauthorized AP.

18. The non-transitory computer readable medium of claim 16, wherein the method further comprises:
  installing and activating a care provider application in the care provider terminal;
  receiving a password of an administrator through a log-in interface of the activated care provider application;
  determining whether or not the received password matches a pre-set password; and
  establishing the AP information of the authorized AP in the care provider terminal.

19. The non-transitory computer readable medium of claim 16, wherein the method further comprises:
  registering an identification and a password of the care provider and a device ID of the care provider terminal to a server to which the care provider terminal is connected via the authorized AP.

* * * * *